United States Patent [19]

Borland et al.

[11] Patent Number: 5,164,120
[45] Date of Patent: Nov. 17, 1992

[54] SURFACTANT MIXTURES

[75] Inventors: James E. Borland; Terry Crutcher; Jeffrey W. Perine; Joe D. Sauer; Kim R. Smith, all of Baton Rouge, La.

[73] Assignee: Ethyl Corporation, Richmond, Va.

[21] Appl. No.: 788,843

[22] Filed: Nov. 7, 1991

Related U.S. Application Data

[63] Continuation-in-part of Ser. No. 698,558, May 10, 1991, abandoned.

[51] Int. Cl.$^5$ ................................. C11D 1/18
[52] U.S. Cl. ...................... 252/546; 252/544; 252/547; 252/548; 252/DIG. 5; 252/DIG. 13; 252/DIG. 14
[58] Field of Search ............... 252/544, 546, 547, 548, 252/DIG. 5, DIG. 13, DIG. 14

[56] References Cited

U.S. PATENT DOCUMENTS 4,555,360 11/1985 Bissett et al. ............... 252/DIG. 13
4,588,522 5/1986 Blaschke et al. .................... 252/547

*Primary Examiner*—Patrick P. Garvin
*Assistant Examiner*—E. D. Irzinski
*Attorney, Agent, or Firm*—Patricia J. Hogan

[57] ABSTRACT

Surfactant mixtures which have foamability performance and/or cost advantages over the individual components consist of 5–85% by weight of an amine oxide corresponding to the formula RR'R"NO in which R is a primary alkyl group containing 6–24 carbons and R' and R" are independently selected from methyl, ethyl, and 2-hydroxyethyl and 95–15% by weight of an alkylamidopropyldimethylbetaine in which the alkyl group contains 8–18 carbons. Preferred mixtures are those in which the amine oxide is N-tetradecyldimethylamine oxide and the betaine is cocoamidopropyldimethylbetaine.

7 Claims, No Drawings

SURFACTANT MIXTURES

CROSS-REFERENCE TO RELATED APPLICATION

This application is a continuation-in-part of copending application Ser. No. 698,558, filed May. 10, 1991, and now abandoned.

FIELD OF INVENTION

This invention relates to surfactant compositions and more particularly to such compositions which are mixtures of amine oxides and betaines.

BACKGROUND

It is known that various surfactants have been found to be useful in cleaning compositions, such as shower gels, shampoos, and light duty detergents (e.g., dish detergents)—compositions in which good foamability is a prerequisite for consumer approval. The surfactants which have been used to the greatest extent in such compositions are anionic surfactants, such as alkyl sulfates, alkyl ether sulfates, sulfonates, sulfosuccinates, and sarcosinates.

Although the use of anionic surfactants in these compositions permits the attainment of desirable characteristics, including good foamability, it would be beneficial to find other surfactants which could provide equal or better performance at a lower cost. However, other known surfactants, such as amine oxides, betaines, and alkanolamides, are either more costly than the anionic surfactants or give poorer performance, e.g., smaller foam volume, when substituted for the anionic surfactants.

It is sometimes advantageous to use mixtures of surfactants in cleaning compositions when the surfactants can serve different functions, e.g., one serving to improve foamability and another serving to adjust viscosity. However, known surfactant mixtures typically provide a compromise between what can be achieved with the surfactant ingredients alone. Thus, e.g., a mixture of (A) a more costly surfactant which provides good foamability by itself with (B) a less expensive surfactant which provides poorer foamability by itself will provide an intermediate foamability.

SUMMARY OF INVENTION

It has been found that a mixture of 5-85% by weight of an amine oxide corresponding to the formula RR'R"NO in which R is a primary alkyl group containing 6-24 carbons and R' and R" are independently selected from methyl, ethyl, and 2-hydroxyethyl and 95-15% by weight of an alkylamidopropyldimethylbetaine in which the alkyl group contains 8-18 carbons provides foamability performance and/or cost advantages over the individual components of the surfactant mixture.

DETAILED DESCRIPTION

Amine oxides which can be used in the practice of the invention are compounds corresponding to the formula RR'R"NO in which R is a primary alkyl group containing 6-24 carbons, preferably 10-18 carbons, and R' and R" are independently selected from methyl, ethyl, and 2-hydroxyethyl. The preferred amine oxides are those in which the primary alkyl group has a straight chain in at least most of the molecules, generally at least 70%, preferably at least 90% of the molecules; and the amine oxides which are especially preferred are those in which R contains 10-18 carbons and R' and R" are both methyl.

Exemplary of the preferred amine oxides are the N-hexyl-, N-octyl-, N-decyl-, N-dodecyl-, N-tetradecyl-, N-hexadecyl-, N-octadecyl-, N-eicosyl-, N-docosyl-, and N-tetracosyldimethylamine oxides, the corresponding amine oxides in which one or both of the methyl groups are replaced with ethyl or 2-hydroxyethyl groups, etc., and mixtures thereof. A particularly preferred amine oxide is N-tetradecyldimethylamine oxide.

Betaines which may be used in admixture with the amine oxides are the alkylamidopropyldimethylbetaines corresponding to the formula $ZC(O)NHC_3H_7(CH_3)_2NCH_2COO^-$ which Z is an alkyl group containing 8-18 carbons. A particularly preferred betaine is cocoamidopropyldimethylbetaine.

The amine oxide/betaine mixtures of the invention are synergistic, i.e., provide foam levels higher than can be achieved by the use of either component alone, when the amine oxide content is anywhere in the range of 5-85% by weight. However, greatest foamability is obtained when the amine oxide content of the mixture is about 20-65% by weight. From the aspect of cost effectiveness, i.e., the cost of preparing any given amount of foam, the preferred mixtures are those containing about 5-75%, more preferably 15-60%, and most preferably 20-50% by weight of the amine oxide.

The invention is advantageous in that it provides novel surfactant mixtures which can provide acceptable levels of foam more economically than the individual components of the mixtures. This characteristic of the mixtures makes them valuable for use in the cleaning compositions which require foaming for customer approval, e.g., shampoos, shower gels, and light duty detergents.

When employed in such compositions, the surfactant mixtures are utilized in an aqueous medium, which typically constitutes about 10-90% of the weight of the compositions; and they may be used in conjunction with other ingredients of the types conventionally used in the compositions. Such ingredients include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following example is given to illustrate the invention and is not intended as a limitation thereof. Unless otherwise specified, quantities mentioned in the example are quantities by weight.

EXAMPLE

Dissolve varying amounts of N-tetradecyldimethylamine oxide and cocoaminopropyldimethylbetaine in hard water (200 ppm as $CaCO_3$) to provide solutions having a total surfactant content of 0.1%. Measure the foamability of the surfactants by (1) placing 30 mL of each of the solutions in a 100 mL stoppered graduated cylinder, (2) inverting the cylinder ten times, (3) measuring the foam height, (4) repeating steps 1-3 twice, and (5) calculating the average of the three measurements. The proportions of amine oxide and betaine used in preparing each of the solutions and the foam heights obtained from them are shown in the table below.

TABLE

| % Amine Oxide | % Betaine | Foam Height (mL) |
| --- | --- | --- |
| 100 | 0 | 33 |
| 85 | 15 | 38 |
| 75 | 25 | 41 |
| 65 | 35 | 43 |
| 60 | 40 | 44 |
| 50 | 50 | 46 |
| 25 | 75 | 45 |
| 20 | 80 | 43 |
| 15 | 85 | 41 |
| 5 | 95 | 38 |
| 0 | 100 | 36 |

What is claimed is:

1. A surfactant mixture consisting of 5-85% by weight of an amine oxide corresponding to the formula RR'R''NO in which R is a primary alkyl group containing 6-24 carbons and R' and R'' are independently selected from the group consisting of methyl, ethyl, and 2-hydroxyethyl and 95-15% by weight of an alkylamidopropyldimethylbetaine in which the alkyl group contains 8-18 carbons.

2. The surfactant mixture of claim 1 wherein R is a primary alkyl group containing 10-18 carbons and R' and R'' are methyl.

3. The surfactant mixture of claim 2 wherein the amine oxide is N-tetrad-decyldimethylamine oxide and the alkylamidopropyldimethylbetaine is cocoamidopropyldimethylbetaine.

4. The surfactant mixture of claim 1 containing about 5-75% by weight of the amine oxide.

5. The surfactant mixture of claim 4 containing about 20-65% by weight of the amine oxide.

6. The surfactant mixture of claim 5 containing about 15-60% by weight of the amine oxide.

7. The surfactant mixture of claim 6 containing about 20-50% by weight of the amine oxide.

* * * * *